United States Patent
Magnuson et al.

(10) Patent No.: US 8,585,680 B2
(45) Date of Patent: Nov. 19, 2013

(54) ENDOVASCULAR DEVICE TIP ASSEMBLY INCORPORATING A MARKER DEVICE AND METHOD FOR MAKING THE SAME

(75) Inventors: Mark A. Magnuson, Bloomington, IN (US); Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1395 days.

(21) Appl. No.: 11/787,626

(22) Filed: Apr. 17, 2007

(65) Prior Publication Data
US 2007/0287957 A1 Dec. 13, 2007

Related U.S. Application Data

(60) Provisional application No. 60/792,779, filed on Apr. 17, 2006.

(51) Int. Cl.
*A61M 25/098* (2006.01)
*B21D 39/00* (2006.01)
*B23P 11/00* (2006.01)
*B23P 13/04* (2006.01)

(52) U.S. Cl.
USPC .................. 604/529; 29/516; 29/521; 29/557

(58) Field of Classification Search
USPC .............. 604/96.01, 103.1, 264, 529; 29/516, 29/521, 557
See application file for complete search history.

(56) References Cited

U.S. PATENT DOCUMENTS

| | | | |
|---|---|---|---|
| 3,605,750 | A | 9/1971 | Sheridan et al. |
| 4,430,083 | A | 2/1984 | Ganz et al. |
| 4,938,220 | A | 7/1990 | Mueller, Jr. |
| 5,034,005 | A | 7/1991 | Appling |
| 5,135,486 | A | 8/1992 | Eberle et al. |
| 5,256,158 | A | 10/1993 | Tolkoff et al. |
| 5,485,667 | A | 1/1996 | Kleshinski |
| 5,489,277 | A | 2/1996 | Tolkoff et al. |
| 5,766,202 | A | 6/1998 | Jones et al. |
| 5,782,810 | A | 7/1998 | O'Donnell |
| 5,820,612 | A * | 10/1998 | Berg .............................. 604/527 |
| 5,899,890 | A | 5/1999 | Chiang et al. |
| 6,179,811 | B1 | 1/2001 | Fugoso et al. |
| 6,221,059 | B1 | 4/2001 | Chiang et al. |
| 6,277,108 | B1 | 8/2001 | McBroom et al. |
| 6,884,235 | B2 | 4/2005 | McGuckin, Jr. et al. |

\* cited by examiner

*Primary Examiner* — Manuel Mendez
*Assistant Examiner* — Nathan R Price
(74) *Attorney, Agent, or Firm* — Brinks Hofer Gilson & Lione

(57) ABSTRACT

An endovascular device tip assembly and method of making the same, incorporating a radiopaque marker usable with catheters and other suitable endovascular devices is provided. The tip assembly incorporates a radiopaque marker device by providing a counterbore within a primary bore of a tubular tip of an endovascular device. The marker device is fitted securely within the counterbore and the tubular tip is further deformed distally of the marker in order to secure the marker within the device.

20 Claims, 2 Drawing Sheets

ENDOVASCULAR DEVICE TIP ASSEMBLY INCORPORATING A MARKER DEVICE AND METHOD FOR MAKING THE SAME

BACKGROUND

This application claims priority to U.S. Provisional Application 60/792,779, filed on Apr. 17, 2006.

The present application relates to an endovascular device tip assembly incorporating a marker and the method of making the same. Moreover, this application relates to the use of a radiopaque marker that is fixed within a medical device, such as a catheter, by counterboring the distal end of a tubular device and placing the marker within.

Endovascular devices have long been known which can be surgically inserted into a body lumen, such as an artery, to reinforce, support, repair, or otherwise enhance the performance of the lumen. For example, catheters generally include a hollow tubular portion, usually formed of resilient plastic, for insertion through the skin of a patient into a cavity, duct or vessel to permit injection or withdrawal of fluids, or to deliver medications to patients for therapeutic reasons. Regardless of the instrument, the accurate placement of the instrument in the patient's body is often critical to its successful use.

As a result, different methods have been developed to help the physician "see" inside of the patient's body and help determine exactly where the endovascular device is being positioned. For example, X-ray, MRI, CT, and ultrasound devices and techniques have been employed. The endovascular devices may still be difficult to position without some enhancement of the device. Medical devices which incorporate radiopaque materials may more accurately position the various medical implements.

Typically, the distal tip of an endovascular device consists of a hollow metal or polymer cylinder which is tapered along the outer surface. The inside diameter of the tip is typically sized to allow the smooth passage of a guidewire of a given diameter. Preferably, the inside diameter remains constant. Therefore, it is desirable to develop a method of incorporating a marker into the tip of an endovascular device without changing the inner diameter of the tip, which would make it more difficult to pass a guidewire therethrough. This invention addresses such a method for incorporating a marker into the tip of an endovascular device.

BRIEF SUMMARY

The endovascular tip device described below may overcome the aforementioned problems and relates to a medical device, and more particularly, to an endovascular tip device assembly and method of making the same that incorporates a radiopaque marker device within the tip assembly.

A method of incorporating a marker into an endovascular device tip is disclosed. This method comprises providing a tubular tip of an endovascular device comprising a distal end portion and at least one longitudinal bore extending therethrough, the distal end portion comprising at least one outlet opening and the at least one longitudinal bore having an internal diameter; creating a counterbore through the distal end portion of the tubular tip, thereby increasing the internal diameter of the at least one longitudinal bore; providing a marker device; positioning the marker device within the counterbore, the marker device having a first end and a second end; and deforming a portion of the tubular tip extending distally beyond the second end of the marker device to retain the marker device within the counterbore.

The method described above wherein the internal diameter of the at least one longitudinal bore is approximately equal to an internal diameter of the marker device.

The method described above wherein the marker device is cylindrically shaped.

The method described above wherein the cylindrical marker device comprises radiopaque material.

The method described above wherein the marker device is about 0.01 to about 0.125 inches in length.

The method as described above, wherein the internal diameter of the counterbore is approximately from about 0.001 inches to about 0.125 inches larger than the internal diameter of the at least one longitudinal bore.

The method described above wherein the internal diameter of the counterbore is approximately 0.004 inches larger than the internal diameter of the at least one longitudinal bore.

The method described above wherein the at least one longitudinal bore is further defined by an outer radial surface and an inner radial surface; and wherein the counterbore is further defined by a first end and a second end defining a ledge between the inner surface of the at least one longitudinal bore and an inner radial surface of the counterbore; and wherein the first end of the marker device is adjacent the ledge.

The method described above, wherein the ledge is approximately 0.0005 to about 0.0625 inches thick and the marker device has a thickness approximately equal to the ledge.

The method described above wherein the ledge is approximately 0.002 inches thick and wherein the marker device has a thickness approximately equal to the ledge.

An endovascular tip device manufactured according to the method as described above.

An endovascular device is disclosed comprising: a tubular tip of the endovascular device having a distal end portion and a proximal end portion, the distal end portion having an internal diameter larger than an internal diameter of the proximal end portion; a radiopaque marker having a first end and a second end and being disposed within the distal end portion; and the distal end portion having a length deformed distally of the second end portion of the radiopaque marker.

The endovascular device described above wherein the length extending beyond the second end of the marker is approximately 0.05 cm to about 2.0 cm.

The endovascular device described above wherein the length extending beyond the second end of the marker device is deformed by heat tapering the length and gradually decreasing the internal diameter of the distal end, securely affixing the marker tubular tip.

The endovascular device described above wherein the tubular tip is formed integrally on a distal end of a catheter body.

The endovascular device described above wherein the tubular tip is bonded on a distal end of a catheter body.

DETAILED DESCRIPTION

An exemplary embodiment of the present invention may be described in use with any endovascular device, but for the purposes of this application, will be referred to as a catheter. To be clear, the tip assembly will be described in accordance with the following method, but other equivalent methods are contemplated by the invention.

Figure 1:
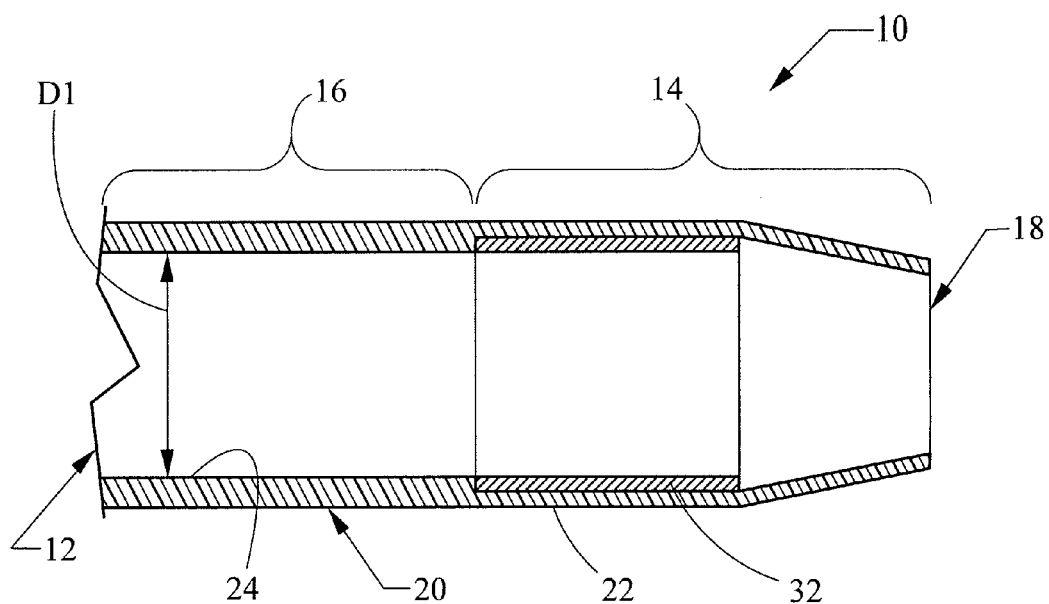
FIG. 1 is side view of the tip of an endovascular device and the marker device in a final configuration of the present invention.

Referring now to FIG. 1, the method of the present invention for incorporating a marker within a tip of an endovascular device, for example a catheter, includes providing a tubular tip 10 of any desired length having a primary bore 12 for directing fluids or mechanical devices, such as stents, to and from the body of the patient. The tubular tip 10 may be integral with the catheter body of a single lumen catheter system, such as a balloon catheter. On catheter based systems that include multiple lumens, the tip may be integral with the innermost lumen. Alternatively, the tubular tip may be glued or heat molded to the outermost catheter body. This technique may result in a larger overall profile of the distal end of the catheter-based system.

Figure 2:
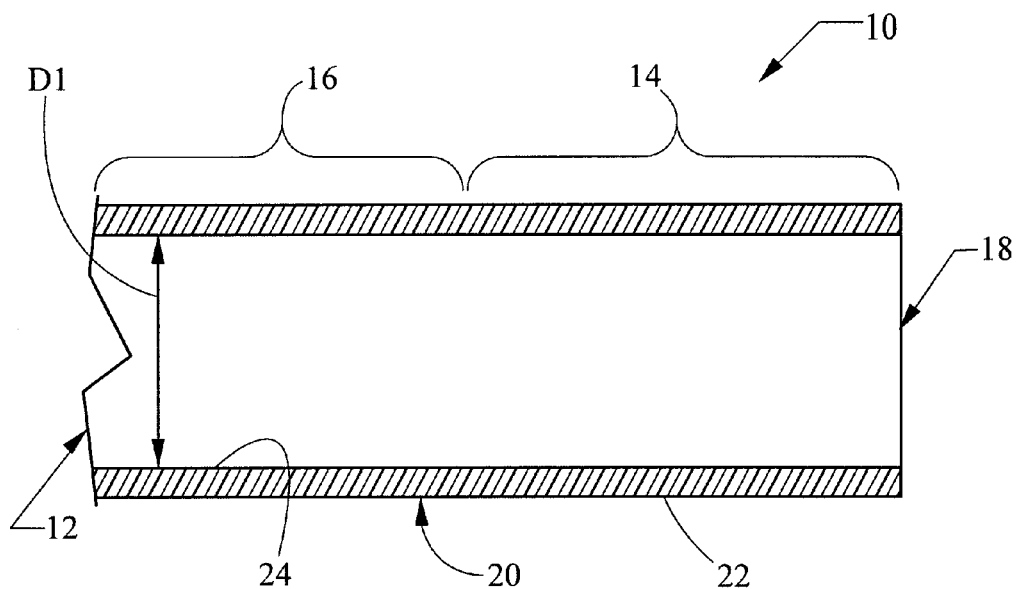
FIG. 2 is side view an endovascular device prior to incorporation of the counterbore.

As shown in FIG. 2, the tubular tip 10 of a catheter body includes a distal end portion 14 and a proximal end portion 16. The distal end portion 14 may define an outlet opening 18 of the primary bore 12. The tubular tip 10 also may include an annular side wall 20 having an outer radial surface 22 and an inner radial surface 24 further defining the bore 12 of the tip 10. The tubular tip 10 of the catheter body may be formed of any appropriate material which may be inserted into the human body, but is preferably formed of a flexible material such as nickel-titanium alloys, polyethylene, nylon, PVC, polyurethane or silicone. The tubular tip 10 may also include various support structures, such as woven or helical reinforcements. The reinforcements may be in the form of wires or bands.

The inner radial surface 24 of the side wall 20 may include a first inner diameter D1. The first inner diameter D1 may generally be between about 0.010 inches to about 0.25 inches, and may desirably be about 0.017 inches wide. Generally, the side wall 20 of the catheter body may be about 0.004 inches thick, measured from the outer radial surface 22 to the inner radial surface 24 of the bore 12. Alternatively, the side wall 20 may range from about 0.001 to about 0.125 inches thick.

Figure 3:
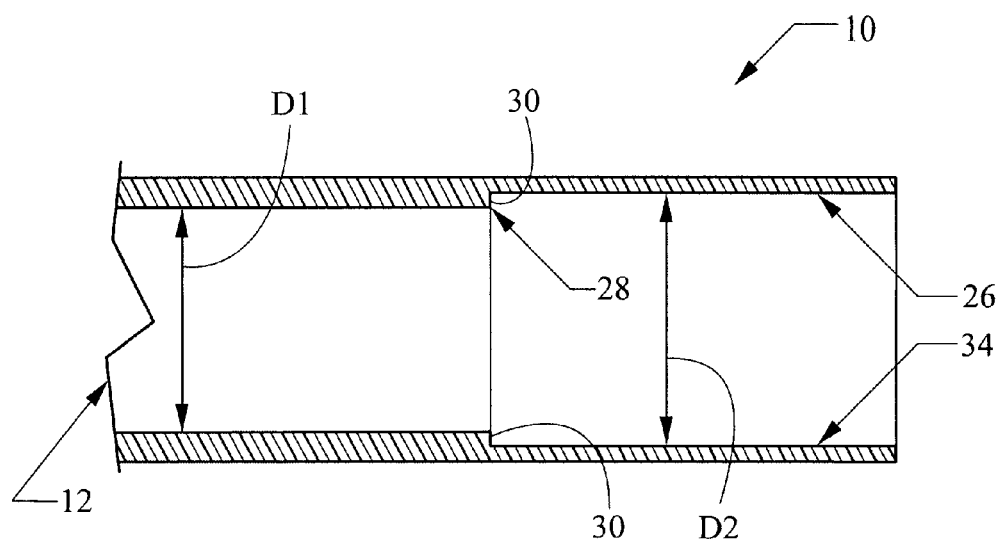
FIG. 3 is side view an endovascular device prior to incorporation of the marker device.

Referring now to FIG. 3, the method further includes forming a counterbore 26 within the tip 10. The counterbore 26 is generally created within the distal end portion 14 of the tubular tip 10. The counterbore 26 may be created in an unmodified tube in a variety of ways. Preferably, but not limited to, the inner radial surface 34 of the bore 12 may be prepared by drilling or grinding the counterbore 26 into the distal end portion 14 of the tubular tip 10. The counterbore 26 may also be formed during the molding process of the catheter body or may be cut or reformed into the tip after the catheter is formed.

Starting at or about the outlet opening 18 of the tip 10, the counterbore 26 may be formed within the annular side wall 20 of the catheter body, lengthwise, toward the proximal end portion 16 of the tubular tip 10. The counterbore 26 provides an enlarged inner diameter, or a secondary inner diameter D2, within a portion of the bore 12. The counterbore 26 may decrease the thickness of the side wall 20 by approximately half of the original wall thickness. One embodiment of the present invention includes a wall thickness of about 0.004 inches. The resulting secondary inner diameter D2 may be about 0.014 to about 0.254 inches, depending on the original thickness of the initial inner diameter of the tip 10. For example, if D1 is originally 0.017 inches, the resulting inner diameter of the bore D2 would be approximately 0.021 inches.

The proximal end 28 of the counterbore 26 generally forms a ledge 30 within the tubular tip 10 of the catheter body. This ledge 30 is generally the same thickness of the marker 32 that is to be incorporated into the tip 10. Such a marker 32 may generally be about 0.002 inches thick. The thickness of the marker and the ledge generally correspond to the size of the counterbore.

Figure 4:
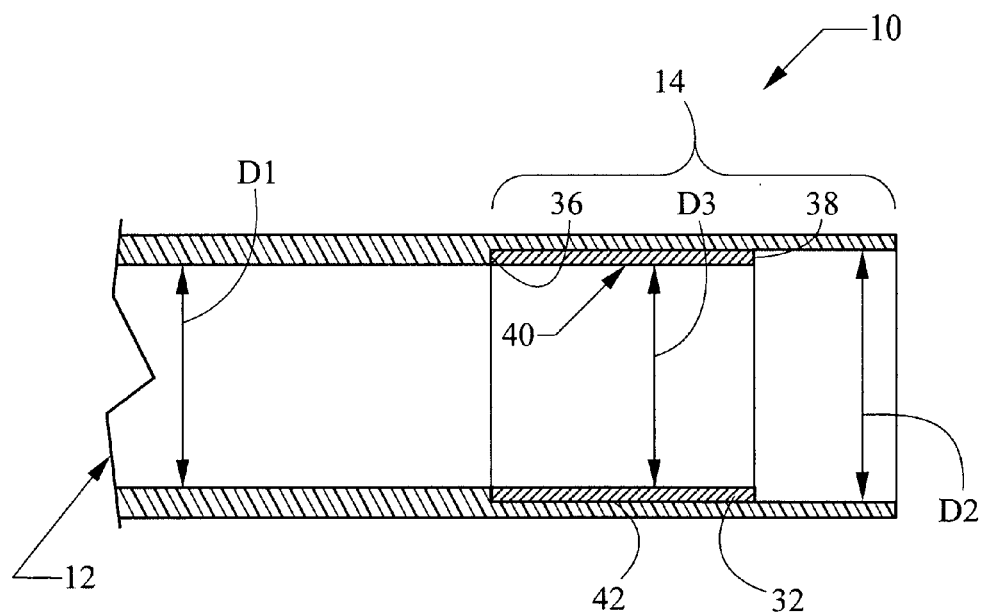
FIG. 4 is side view of the tip of an endovascular device and the marker device in an untapered configuration.

Referring now to FIG. 4, the method further includes providing a cylindrical band, marker 32, formed of a radiopaque, or other suitable, material having an outer diameter D3 which generally corresponds to the secondary inner diameter D2 of the tubular tip 10 as defined by the inner radial surface 34 of the counterbore 26, and an inner diameter DA4, generally corresponding to D1. The marker 32 may be formed of an x-ray reflective, or radiopaque, material which may be viewed by the physician via radiography, fluoroscopy, or other usual visualization techniques. The marker may be a cylindrical metal sleeve, formed of palladium, iridium, gold, tantalum, tungsten, platinum, or other suitable radiopaque material. It is also contemplated that the marker may be a radiopaque polymer, such as radiopaque nylon. Bismuth, barium, and tungsten are examples of suitable fillers that may be used to make polymers radiopaque.

Preferably, the marker is a cylindrical sleeve, but it also may be a split cylinder, a half moon shape, a radiopaque ring, or other suitable shape that would allow the marker to be friction fit or otherwise secured within the counterbore of the tubular tip.

The marker 32 is incorporated into the catheter body within the distal end portion 14 of the tip 10 so as to accurately mark the position of the distal end of the catheter when exposed to x-rays. The marker 32 may be a cylindrical band having an outer radial surface 42 and an inner radial surface 40 defining a center bore which terminates at a first end 36 and at a second, opposite end 38. The first end 36 of the marker 32 may be manually positioned adjacent the ledge 30 of the counterbore 26 so that the inner radial surface 40 of the cylindrical marker 32 extends no further radially inward than the inner radial surface 24 of the bore 12 of the tubular tip 10 of the catheter body. As a result, the inner radial surface 24 of the bore 12 is substantially constant without interruptions or inwardly extending ridges formed by the first 36 and second ends 38 of the cylindrical marker 32. The marker may also be placed within the counterbore by use of an automated machine, and it may be molded in to the counterbore upon formation of the tip.

Because the inner radial surface 24 of the tip 10 remains substantially constant, it prevents the formation of internal restrictions in the primary bore 12 thereby maintaining a constant inner diameter D1 and D4.

Also, because the marker 32 is positioned within the inner radial surface 24 of the tip 10, the outer radial surface 22 may remain smooth. A smooth outer radial surface 22 is advantageous on many medical instruments that are to be inserted into a patient's body since the outer surface slides against the patient's skin and internal tissue. A smooth outer surface 22 allows the medical instrument to more easily be pushed through a patient's skin or other openings with small clearances while minimizing harm to the patient.

Referring again to FIG. 1, in order to securely incorporate the marker 32 of the present invention into the catheter body, the method of the present invention further includes deforming or tapering the distal end portion 14 of the tip 10 that extends beyond the second end 38 of the marker 32. One way to taper the tip 10 is by heating and/or applying pressure to the distal end portion 14. The tip 10 may be reformed to a desired diameter, generally accommodating the diameter of the wire guide to be used with the device. The wall of the tip 10 may also be formed around the marker 32 so that a portion of the wall abuts the second end 38 of the marker 32, further securing the marker 32 within the device.

In use, the tubular tip 10 of the endovascular device is inserted into a patient's body to perform one or more of a variety of functions including the delivery and withdrawal of fluids and mechanical devices such as stents. As is apparent, the present invention may be used to incorporate radiopaque markers 32 formed of various suitable materials in to many different types of endovascular devices including delivery catheters, angioplasty balloons and other endoscopic instrumentation.

When the device is positioned in the patient's body and the body is exposed to x-rays, the radiopaque marker 32 provides a clear indication to the physician as to the precise location of the marked portion of the instrument. The marker 32 may also be provided with indicia marked or etched into the outer surface of the band. These indicia may be visible when exposed to x-rays during use so as to assist the physician in the procedure by, for example, distinguishing the catheter from an adjacent catheter.

It is therefore intended that the foregoing detailed description be regarded as illustrative rather than limiting, and that it be understood that it is the following claims, including all equivalents, that are intended to define the spirit and scope of this invention.

The invention claimed is:

1. A method of incorporating a marker into an endovascular device tip comprising:
providing a tubular tip of an endovascular device comprising a distal end portion and at least one longitudinal bore extending therethrough, said distal end portion comprising an annular side wall and at least one outlet opening, wherein said side wall includes an outer radial surface and an inner radial surface defining a radial wall thickness, and said at least one longitudinal bore is defined by an internal diameter;
removing a portion of material from the inner radial surface of the side wall to create a counterbore within the side wall and through said distal end portion, thereby increasing the internal diameter of said at least one longitudinal bore and decreasing the thickness of said side wall;
providing a marker device;
positioning said marker device within said counterbore, said marker device having a first end and a second end; and
deforming a portion of said tubular tip extending distally beyond said second end of said marker device to retain said marker device within said counterbore.

2. The method of claim 1, wherein said internal diameter of said at least one longitudinal bore is approximately equal to an internal diameter of the marker device.

3. The method of claim 1, wherein said marker device is cylindrically shaped.

4. The method of claim 3, wherein said marker device comprises radiopaque material.

5. The method of claim 1, wherein said marker device is about 0.01 to about 0.125 inches in length.

6. The method of claim 1, wherein said internal diameter of said counterbore is approximately from about 0.001 inches to about 0.125 inches larger than said internal diameter of said at least one longitudinal bore.

7. The method of claim 6, wherein said internal diameter of said counterbore is approximately 0.004 inches larger than said internal diameter of said at least one longitudinal bore.

8. The method of claim 1, wherein said counterbore is further defined by a first end and a second end defining a ledge between said inner radial surface of said at least one longitudinal bore and an inner surface of the counterbore; and
wherein said first end of the marker device is positioned adjacent said ledge.

9. The method of claim 8, wherein said ledge is approximately 0.0005 to about 0.0625 inches thick and said marker device has a radial thickness approximately equal to said ledge.

10. The method of claim 9, wherein said ledge is approximately 0.002 inches thick and said marker device has a radial thickness approximately equal to said ledge.

11. An endovascular tip device manufactured according to the method of claim 1.

12. The method of claim 1, wherein the counterbore is formed by drilling or grinding into the distal end portion of the tubular tip.

13. The method of claim 1, wherein the tubular tip comprises a catheter body and the counterbore is formed by a molding process of the catheter body.

14. The method of claim 1, wherein the marker device is positioned within the inner radial surface of the tubular tip so that the outer diameter of the distal end portion surrounding the marker device remains substantially unchanged following said positioning of the marker device.

15. An endovascular device, comprising:
a tubular tip of said endovascular device comprising a distal end portion and a proximal end portion, said distal end portion having a first portion and a second portion, said first portion of said distal end portion having an internal diameter larger than an internal diameter of said proximal end portion;
a radiopaque marker having a first end and a second end and being disposed within said first portion of the distal end portion, said second portion of the distal end portion being deformed distally of the second end of the radiopaque marker; and,
wherein each of said proximal and distal end portions comprises an annular side wall, the proximal annular side wall having a first radial wall thickness, the distal annular side wall having a second radial wall thickness less than the first radial wall thickness, wherein both the first and second portions of the distal end portion comprise the second radial wall thickness.

16. The endovascular device of claim 15, wherein said second portion of the distal end portion extending beyond said second end of said marker is approximately 0.05 cm to about 2.0 cm.

17. The endovascular device of claim 15, wherein said second portion of the distal end portion extending beyond said second end of said marker device is deformed by heat tapering said second portion and gradually decreasing said internal diameter of said second portion, securely affixing said marker device to said tubular tip.

18. The endovascular device of claim 15, wherein said tubular tip is formed integrally on a distal end of a catheter body.

19. The endovascular device of claim 15, wherein said tubular tip is bonded on a distal end of a catheter body.

20. The endovascular device of claim 15, wherein the distal annular side wall portion is tapered to create an outlet opening having a reduced outer diameter relative to the outer diameter of the proximal end portion.

* * * * *

UNITED STATES PATENT AND TRADEMARK OFFICE
CERTIFICATE OF CORRECTION

| | | |
|---|---|---|
| PATENT NO. | : 8,585,680 B2 | Page 1 of 1 |
| APPLICATION NO. | : 11/787626 | |
| DATED | : November 19, 2013 | |
| INVENTOR(S) | : Magnuson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1505 days.

Signed and Sealed this
Third Day of March, 2015

Michelle K. Lee
*Deputy Director of the United States Patent and Trademark Office*